US008329902B2

(12) United States Patent
Li et al.

(10) Patent No.: US 8,329,902 B2
(45) Date of Patent: Dec. 11, 2012

(54) OPTICALLY PURE DIHYDROPYRIMIDINE COMPOUNDS AND THEIR USES FOR THE PREPARATION OF A MEDICAMENT FOR TREATMENT AND PREVENTION OF VIRAL DISEASES

(75) Inventors: Song Li, Beijing (CN); Guangqiang Xia, Beijing (CN); Guoming Zhao, Beijing (CN); Lili Wang, Beijing (CN); Zhibing Zheng, Beijing (CN); Yunde Xie, Beijing (CN); Wu Zhong, Beijing (CN); Junhai Xiao, Beijing (CN); Xingzhou Li, Beijing (CN); Hao Cui, Beijing (CN)

(73) Assignee: Beijing Molecule Science And Technology Co., Ltd., Beijing (CN)

( * ) Notice: Subject to any disclaimer, the term of this patent is extended or adjusted under 35 U.S.C. 154(b) by 509 days.

(21) Appl. No.: 12/373,101
(22) PCT Filed: Jul. 9, 2007
(86) PCT No.: PCT/CN2007/002099
§ 371 (c)(1),
(2), (4) Date: Mar. 6, 2009
(87) PCT Pub. No.: WO2008/009210
PCT Pub. Date: Jan. 24, 2008

(65) Prior Publication Data
US 2010/0004268 A1    Jan. 7, 2010

(30) Foreign Application Priority Data
Jul. 10, 2006 (CN) .......................... 2006 1 0098645

(51) Int. Cl.
C07D 239/02    (2006.01)
C07D 239/00    (2006.01)
C07D 401/00    (2006.01)
(52) U.S. Cl. ..................... 544/335; 544/242; 544/333
(58) Field of Classification Search .................. 544/333
See application file for complete search history.

(56) References Cited

U.S. PATENT DOCUMENTS

| 3,778,474 | A | * | 12/1973 | Stocker | .......................... 564/199 |
| 6,503,913 | B1 | | 1/2003 | Goldmann et al. | |
| 6,696,451 | B1 | * | 2/2004 | Stoltefuss et al. | ............ 514/256 |
| 2004/0167135 | A1 | | 8/2004 | Stoltefuss et al. | |

FOREIGN PATENT DOCUMENTS

| EP | 0288628 A1 | 11/1988 |
| JP | 63-142251 A * | 6/1988 |
| JP | 2002-512243 A | 4/2002 |
| JP | 2002-512244 A | 4/2002 |
| JP | 2009-542729 A | 12/2009 |
| WO | 9954326 A1 | 10/1999 |
| WO | 9954329 A1 | 10/1999 |
| WO | 2006009889 A1 | 1/2006 |

OTHER PUBLICATIONS

Kuno et al. "Studies on cerebral protection Agent II Novel 4-arylpyrimidien with anti-anoxic and anti-lipid peroxidation activities," Chem. Pharm. Bull. 1992, vol. 49, No. 9, pp. 2423-2431.*

English abstract of JP 63-142251A.*
Inhibition of Hepatitis B Virus Replication by Drug-Induced Depletion of Nucleocapsids, Karl Deres et al., Science, vol. 299, pp. 893-896 (2003).
Tunable Carbon-Carbon and Carbon-Sulphur Cross-Coupling of Boronic Acids With 3,4-Dihydropyrimidine-2-thiones, Alenka Lengar et al., Organic Letters, vol. 6, No. 5, pp. 771-774 (2004).
Japanese Office Action for Application No. 2009-518703, (Jul. 8, 2011).
Deres, "Inhibition of Hepatitis B Virus Replication by Drug-Induced Depletion of Nucleocapsids", Science, 2003, vol. 299, pp. 893-896.
Weber, "Inhibition of Human Hepatitis B Virus (HBV) by a Novel Non-Nucleosidic Compound in a Transgenic Mouse Model", Antiviral Research, 2002, vol. 54, pp. 69-78.
Suzuki, "Design and Synthesis of Non-Hydroxamate Histone Deacetylase Inhibitors:Identification of a Selective Histone Acetylating Agent", Bioorganic & Medicinal Chemistry, 2005, vol. 13, pp. 4332-4342.
Jones, "Analogues of Thiolactomycin as Potential Antimalarial Agents", Journal of Medical Chemistry, 2005, vol. 48, pp. 5932-5941.
Bandgar, "Chemoselective Transesterification of β-Keto Esters Under Neutral Conditions Using NBS as a Catalyst", Synlett, 2001, vol. 11, pp. 1715-1718.
Kumar, "A Facile and Selective Procedure for Transesterification of β-Keto Esters Promoted by Yttria-Zirconia Based Lewis Acid Catalyst", Synlett, 2000, vol. 2, pp. 251-253.
Garcia, "Lipase-Catalyzed Aminolysis and Ammonolysis of β-Ketoesters. Synthesis of Optically Active β-ketoamides", Tetrahedron, 1994, vol. 50, No. 23, pp. 6935-6940.
Witzeman, "Transacetoacetylation with tert-Butyl Acetoacetate: Synthetic Applications", Journal of Organic Chemistry, 1991, vol. 56, pp. 1713-1718.
Jones, "Metallation of 3-Acetyltetramic Acids: A New Synthesis of 3-Dienoyl- and 3-Trienoyl-tetramic Acids", Tetrahedron Letters, 1987, vol. 28, No. 14, pp. 1565-1568.
D'Angeli, "The Acetoacetyle Group, an Amino Protective Group of Potential Use in Peptide Synthesis", Tetrahedron Letters, 1965, vol. 10, pp. 605-608.
European Search Report dated Nov. 3, 2011 for Application No. 07764007.6 (PCT/CN2007/002099).

* cited by examiner

Primary Examiner — Shengjun Wang
(74) Attorney, Agent, or Firm — MacMillan, Sobanski & Todd, LLC

(57) ABSTRACT

The present invention relates to an optically pure compound of formula (I) or a pharmaceutically acceptable salt or hydrate thereof, a process for preparing the optically pure compound of formula (I), and use of the optically pure compound of formula (I) or a pharmaceutically acceptable salt or hydrate thereof as a medicament, in particular as a medicament for the treatment and prevention of type B hepatitis.

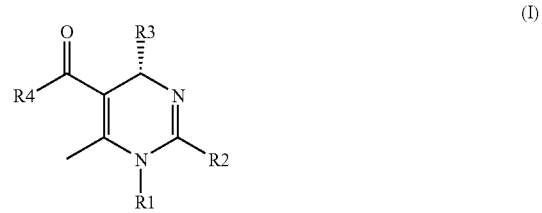

(I)

3 Claims, No Drawings

OPTICALLY PURE DIHYDROPYRIMIDINE COMPOUNDS AND THEIR USES FOR THE PREPARATION OF A MEDICAMENT FOR TREATMENT AND PREVENTION OF VIRAL DISEASES

TECHNICAL FIELD

The present invention relates to an optically pure dihydropyrimidine compound of formula (I) and a process for preparing the same, and a pharmaceutical composition comprising the compound, as well as use of the compound or a pharmaceutically acceptable salt thereof or a hydrate thereof as a medicament, in particular as a medicament for the treatment and prevention of type B hepatitis.

BACKGROUND ART

Chronic type B hepatitis is a serious infectious disease caused by hepatitis B virus (HBV) and prevalent throughout the world, and is closely relevant to the occurrence of hepatic cirrhosis and liver cancer. China is a high-risk area of type B hepatitis. The results of seroepidemiological survey of viral hepatitis in China from 1992 to 1995 showed that the persons carrying hepatitis B virus surface antigen (HBsAg) in China accounted for 9.7% of the population, and it was estimated that about $1.3 \times 10^8$ persons were HBV carriers. The study on the epidemiological situation of viral hepatitis in China demonstrated that the annual reported incidence of HB was increased from 21.9/100 thousands in 1990 to 53.3/100 thousands in 2003, showing an obvious ascending tendency (Wang Xiaojun, Zhang Rongzhen, Hu Yuansheng, et al, Surveillance of Diseases, 2004, 19(8): 290-292). Chronict type B hepatitis not only seriously affects human health, but also imposes heavy economic burden on family and society, and has become one of important public health problems in China.

The drugs useful for treating chronic type B hepatitis mainly include two varieties—immunomodulator and nucleoside DNA polymerase inhibitor (Loomba R., Liang T. J., Antivir. Ther., 2006, 11(1): 1-15). The former includes: interferon-α2b (IFN-α2b, Intron A®) and PEGylated interferon-α2a (peg-IFN-α2a, Pegasys®); the latter includes: Lamivudine (Epivir-HBV®), Adefovir Dipivoxil (Hepsera®) and Entecavir (Baraclude®). Comparatively speaking, the drugs capable of being used in clinical application for treating type B hepatitis still have quite few types and quantities. Thus, it is highly important to continuously develop new safe and effective anti-virus drugs, in particular drugs having totally new mechanism of action.

Deres et al reported heteroaromatic ring substituted dihydropyrimidine (HAP) compounds represented by Bay 41-4109, Bay 39-5493, which could take the effect of suppressing HBV replication through preventing the formation of normal nucleocapsid. The binding of this kind of compounds with core protein had structural specificity (Deres K., Schroder C. H., Paessens A., et al. Science, 2003, 299 (5608): 893-896). The study on its mechanism of action showed that through the action with 113-143 amino acid residues of core protein, HAP changed the angle between dimers forming nucleocapsid, thereby forming unstable swelled nucleocapsid, and accelerating the degradation of core protein (Hacker H. J., Deres K., Mildenberger M., et al. Biochem. Pharmacol. 2003, 66(12): 2273-2279). WO99/54326 and WO99/54329 respectively disclosed dihydropyrimidine compounds substituted by 2-pyridyl group and 2-thiazolyl group.

CONTENTS OF THE INVENTION

The present invention relates to an optically pure dihydropyrimidine compound of formula (I)

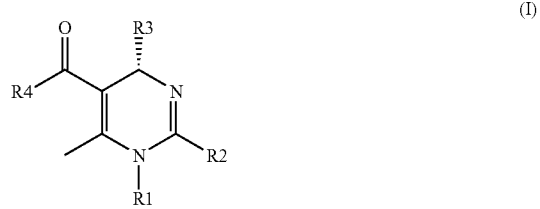

or a pharmaceutically acceptable salt or hydrate thereof, wherein $R^1$ represents hydrogen, $(C_1-C_4)$-allyl, $(C_2-C_4)$-alkenyl, $(C_1-C_6)$-acyl, arylacyl, or arylsulfonyl, $R^2$ represents phenyl, thiazolyl, or imidazolyl optionally substituted up to 5 times by one or more substituents, the same or different, selected from: halogen, hydroxyl, cyano, trifluoromethyl, nitro, benzyl, $(C_1-C_6)$-alkyl, $(C_1-C_6)$-alkoxy, $(C_1-C_6)$-allylthio, $(C_1-C_6)$-alkoxycarbonyl, $(C_1-C_6)$-acyloxy, amino, $(C_1-C_6)$-alkylamino, $(C_1-C_6)$-dialkylamino, or $(C_1-C_6)$-acylamino, $R^3$ represents phenyl, furyl, thienyl, triazolyl, pyridyl, or cycloalkyl having 3 to 6 carbon atoms, wherein the above ring systems may be optionally mono- or multi-substituted by one or more substituents, the same or different, selected from: halogen, trifluoromethyl, trifluoromethoxy, trifluoromethylsulfonyl, nitro, cyano, carboxy, hydroxyl, $(C_1-C_6)$-alkoxy, $(C_1-C_6)$-alkoxycarbonyl and $(C_1-C_6)$-allyl, wherein said allyl may be substituted by aryl having from 6 to 10 carbon atoms, halogen, or a group represented by formula $—S—R^5$, $NR^6R^7$, $CO—NR^8R^9$ or $-A-CH_2—R^{10}$, wherein $R^5$ represents phenyl optionally substituted by halogen, $R^6$, $R^7$, $R^8$ and $R^9$, the same or different, respectively represent hydrogen, phenyl, hydroxyl-substituted phenyl, hydroxyl, $(C_1-C_6)$-acyl or $(C_1-C_6)$-alkyl, wherein said alkyl may be substituted by hydroxyl, $(C_1-C_6)$-alkoxycarbonyl, phenyl or hydroxyl-substituted phenyl, A represents O, S, SO or $SO_2$, $R^{10}$ represents phenyl optionally mono- or multi-substituted by one or more substituents, the same or different, selected from: halogen, nitro, trifluoromethyl, $(C_1-C_6)$-allyl and $(C_1-C_6)$-alkoxy, $R^4$ represents a group represented by formula $—OR^{11}$ or

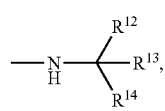

wherein $R^{11}$ represents hydrogen, a straight, branched or cyclic, saturated or unsaturated $(C_1-C_8)$-hydrocarbyl, wherein said hydrocarbyl optionally comprises one or two identical or different heterochain unit(s) selected from the group consisting of O, CO, NH, $—NH(C_1-C_4)$-allyl, $—N((C_1-C_4)$- alkyl)$_2$, S and SO$_2$, and is optionally substituted by halogen, nitro, cyano, alkoxy, aryl having from 6 to 10 carbon atoms, aralkyl, heteroaryl or a group represented by formula —NR$^{15}$R$^{16}$ wherein R$^{15}$ and R$^{16}$, the same or different, respectively represent hydrogen, benzyl or (C$_1$-C$_6$)-alkyl, R$^{12}$, R$^{13}$ and R$^{14}$ are different and respectively represent a substituent selected from: hydrogen, halogen, nitro, cyano, C$_{1-6}$ alkoxycarbonyl, aryl, a straight, branched or cyclic, saturated or unsaturated (C$_1$-C$_8$)-hydrocarbyl, wherein said hydrocarbyl is optionally substituted by halogen, nitro, cyano, C$_{1-6}$ alkoxy, C$_{1-6}$ alkoxycarbonyl, aryl having from 6 to 10 carbon atoms, aryl C$_{1-6}$ alkyl, heteroaryl.

In the present specification, (C$_2$-C$_6$)-alkenyl refers to a straight or branched alkenyl having from 2 to 6 carbon atoms, preferably a straight or branched alkenyl having from 3 to 5 carbon atoms, including, but not limited to, vinyl, propenyl, n-pentenyl, n-hexenyl.

In the present specification, (C$_1$-C$_6$)-acyl refers to a straight or branched acyl having from 1 to 6 carbon atoms, preferably a straight or branched acyl having from 2 to 4 carbon atoms, including, but not limited to, formyl, acetyl.

In the present specification, aryl usually refers to a 5- to 14-membered substituted or unsubstituted aryl ring system, or an aryl ring system comprising a fused bicycle or tricycle, including, but not limited to, phenyl and naphthyl.

In the present specification, (C$_1$-C$_6$)-allyl refers to a straight or branched radical having from 1 to 6 carbon atoms, including, but not limited to methyl, ethyl, n-propyl, isopropyl, n-butyl, sec-butyl, isobutyl, t-butyl, and etc.

In the present specification, (C$_1$-C$_6$)-alkoxy refers to a straight or branched alkoxy having from 1 to 6 carbon atoms, preferably a straight or branched alkoxy having from 1 to 4 carbon atoms, including, but not limited to methoxy, ethoxy, propoxy, isopropoxy, butoxy, isobutoxy, t-butoxy, and etc.

In the present specification, (C$_1$-C$_6$)-allylthio refers to a straight or branched alkylthio having from 1 to 6 carbon atoms, preferably a straight or branched allylthio having from 1 to 4 carbon atoms.

In the present specification, (C$_1$-C$_6$)-alkoxycarbonyl refers to a straight or branched alkoxycarbonyl having from 1 to 6 carbon atoms, preferably a straight or branched alkoxycarbonyl having from 1 to 4 carbon atoms, including, but not limited to methoxycarbonyl, ethoxycarbonyl, propoxycarbonyl, isopropoxycarbonyl, butoxycarbonyl, isobutoxycarbonyl, t-butoxycarbonyl, and etc.

In the present specification, chiral primary amine refers to primary amines at least including one chiral center, in R-configuration or S-configuration, which includes, but not limited to, (R) or (S)-1-phenylethylamine, (R) or (S)-1-phenylpropylamine, (R) or (S)-1-(2-naphthyl)ethylamine, D or L natural or non-natural amino acids.

The compound of the present invention may exist in stereometric forms.

The compound of the present invention includes a compound of the formula (I) and its isomer Ia and a mixture thereof. If R$^1$ is hydrogen, isomers I and Ia exist in tautomeric equilibrium:

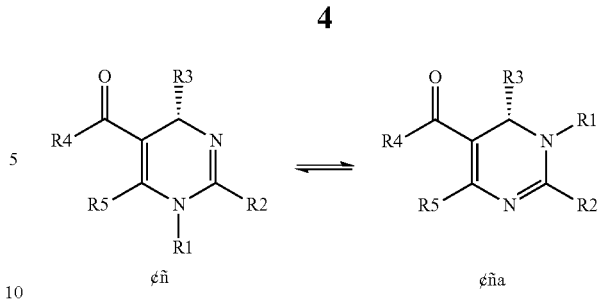

The compound of the present invention may also be in the form of a salt. The preferred pharmaceutically acceptable salt includes, but not limited to, salts formed with various inorganic acids such as hydrochloric acid, sulfuric acid, phosphoric acid, phosphorous acid, hydrobromic acid and nitric acid, and salts formed with various organic acids such as maleic acid, fumaric acid, malic acid, succinic acid, tartaric acid, citric acid, acetic acid, lactic acid, benzoic acid, methanesulfonic acid, ethanesulfonic acid, benzenesulfonic acid, p-toluenesulfonic acid, palmic acid and etc.

The pharmaceutically acceptable salt further includes, but not limited to, metal salts of the compound of the present invention, such as sodium salt, potassium salt, magnesium salt or calcium salt, or ammonium salts formed with ammonia or an organic amine such as ethylamine, diethylamine, triethylamine, diethanolamine, triethanolamine, dicyclohexylamine, dimethylaminoethanol, arginine, lysine, ethylenediamine, or 2-phenylethylamine, and etc.

Some compounds in the present invention may be crystallized or recrystallized by using water or various organic solvents, and in this case, various solvates may be formed. The present invention includes those stoichiometric solvates, hydrates, and also compounds comprising variable amount of water formed when prepared using lyophilisation.

The compounds of formula (I) as defined below and their salts or hydrates are preferred, wherein:

R$^1$ represents hydrogen, methyl, formyl, acetyl, arylacyl, arylsulfonyl,

R$^2$ represents phenyl substituted by halogen for up to 5 times, or thiazolyl, imidazolyl substituted up to 3 times by one or more substituents, the same or different, selected from: fluoro, chloro, bromo, benzyl, (C$_1$-C$_4$)-alkyl, (C$_1$-C$_4$)-alkoxy, amino, (C$_1$-C$_4$)-acylamino, R$^3$ represents phenyl, furyl, thienyl, pyridyl, cyclopentyl or cyclohexyl, wherein the above ring systems may be optionally mono- or multi-substituted by one or more substituents, the same or different, selected from: halogen, trifluoromethyl, trifluoromethoxy, trifluoromethylsulfonyl, nitro, cyano, carboxy, hydroxyl, methoxycarbonyl, and a group represented by formula —CONHCH$_2$C(CH$_3$)$_3$, —CONH(CH$_2$)$_2$OH, —CONHCH$_2$C$_6$H$_5$, CONHC$_6$H$_5$, —OCH$_2$C$_6$H$_5$ or —S-pCl—C$_6$H$_4$, R$^4$ represents a group represented by formula —OR$^{11}$ or

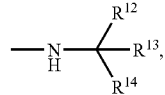

wherein

R$^{11}$ represents hydrogen, (C$_1$-C$_4$)-alkenyl or (C$_1$-C$_4$)-alkyl, wherein the radical may be optionally substituted by halogen, pyridyl, cyano, phenoxy, alkoxy, trifluoroethyl, benzyl or a group represented by formula —NR$^{15}$R$^{16}$, wherein R$^{15}$ and R$^{16}$, the same or different, respectively represent hydrogen, benzyl or (C$_1$-C$_4$)-alkyl, R$^{12}$, R$^{13}$ and R$^{14}$ are different and respectively represent a substituent selected from: hydrogen, fluoro, chloro, nitro, cyano, alkoxycarbonyl, aryl, a straight, branched or cyclic, saturated or unsaturated (C$_1$-C$_6$)-hydrocarbyl, wherein said hydrocarbyl is optionally substituted by halogen, nitro, cyano, alkoxy, alkoxycarbonyl, aryl having from 6 to 10 carbon atoms, arylalkyl, heteroaryl.

The compounds of formula (I) as defined below and their salts or hydrates are particularly preferred, wherein:

R$^1$ represents hydrogen, methyl, formyl, acetyl, benzoyl, phenylsulfonyl, p-toluene sulfonyl, R$^2$ represents phenyl substituted by fluoro for up to 5 times, or thiazolyl or imidazolyl substituted up to 2 times by one or more substituents, the same or different, selected from: fluoro, chloro, bromo, benzyl, (C$_1$-C$_3$)-alkyl, (C$_1$-C$_3$)-alkoxy, amino, (C$_1$-C$_3$)-acylamino, R$^3$ represents phenyl, furyl, thienyl, pyridyl, cyclopentyl or cyclohexyl, wherein the above ring systems may be optionally substituted up to 3 times by one or more substituents, the same or different, selected from: fluoro, chloro, bromo, iodo, hydroxyl, trifluoromethyl, trifluoromethoxy, trifluoromethylsulfonyl, nitro, cyano, carboxy, methoxycarbonyl, and a group represented by formula —CONHCH$_2$C(CH$_3$)$_3$, —CONH(CH$_2$)$_2$OH, —CONHCH$_2$C$_6$H$_5$, —CONHC$_6$H$_5$, —OCH$_2$C$_6$H$_5$ or —S-pCl—C$_6$H$_4$, R$^4$ represents a group represented by formula —OR$^{11}$ or

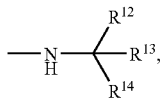

wherein

R$^{11}$ represents hydrogen, (C$_1$-C$_3$)-alkenyl or (C$_1$-C$_4$)-allyl, wherein the radical may be optionally substituted by halogen, pyridyl, cyano, phenoxy, alkoxy, trifluoroethyl, benzyl or a group represented by formula —NR$^{15}$R$^{16}$, wherein R$^{15}$ and R$^{16}$, the same or different, respectively represent hydrogen, benzyl or methyl, R$^{12}$, R$^{13}$ and R$^{14}$ are different and respectively represent a substituent selected from: hydrogen, alkoxycarbonyl, substituted or unsubstituted phenyl, naphthyl, benzyl, a straight or branched (C$_1$-C$_3$)-hydrocarbyl.

The compounds of formula (I) as defined below and their salts or hydrates are especially particularly preferred, wherein:

R$^1$ represents hydrogen or acetyl,

R$^2$ represents phenyl substituted up to 3 times by fluoro, or 2-thiazolyl, 4-thiazolyl, 5-thiazolyl, or 2-imidazolyl substituted up to 2 times by one or more substituents, the same or different, selected from: fluoro, chloro, methyl, benzyl, amino, acetylamino, R$^3$ represents phenyl substituted up to 3 times by one or more substituents, the same or different, selected from: fluoro, chloro, bromo, hydroxyl, nitro, methoxy, or methyl, R$^4$ represents a group represented by formula —OR$^{11}$ or

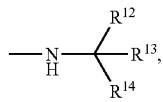

wherein

R$^{11}$ represents a linear or branched allyl having up to 3 carbon atoms, which may be substituted by fluorine or chlorine atom, R$^{12}$ and R$^{14}$ are different and respectively represent a substituent selected from: hydrogen, methyl, ethyl, propyl, methoxycarbonyl, ethoxycarbonyl, or phenyl.

The particularly preferred compounds of formula (I) are the following compounds:

1) (R,R)—N-(1-phenylethyl)-4-(2-chloro-4-fluorophenyl)-6-methyl-2-(2-thiazolyl)-1,4-dihydropyrimidin-5-carboxamide;

2) Ethyl (R)-4-(2-chloro-4-fluorophenyl)-6-methyl-2-(2-thiazolyl)-1,4-dihydropyrimidin-5-carboxylate;

3) Trifluoroethyl (R)-4-(2-chloro-4-fluorophenyl)-6-methyl-2-(2-thiazolyl)-1,4-dihydropyrimidin-5-carboxylate;

4) (R,R)—N-(1-phenylethyl)-4-(2-chloro-4-fluorophenyl)-6-methyl-2-(2,4,6-trifluorophenyl)-1,4-dihydropyrimidin-5-carboxamide;

5) Ethyl (R)-4-(2-chloro-4-fluorophenyl)-6-methyl-2-(2,4,6-trifluorophenyl)-1,4-dihydro-pyrimidin-5-carboxylate;

6) (S,R)—N-(1-phenylethyl)-4-(2-chloro-4-fluorophenyl)-6-methyl-2-(5-thiazolyl)-1,4-dihydropyrimidin-5-carboxamide; and 7) Ethyl (R)-4-(2-chloro-4-fluorophenyl)-6-methyl-2-(5-thiazolyl)-1,4-dihydropyrimidin-5-carboxylate, or their pharmaceutically acceptable salts or hydrates.

The compound of formula (I) in the present invention may be prepared by the following process:

1) in the presence or absence of a base or acid, and in a suitable inert solvent, reacting an amidine of formula (II) or a salt thereof

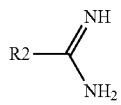

(II)

wherein R$^2$ is defined as above, with an aldehyde of formula (III)

(III)

wherein R$^3$ is defined as above, and a compound of formula (IV)

(□)

wherein R$^{12}$, R$^{13}$, R$^{14}$ are defined as above, to obtain a compound of formula (V)

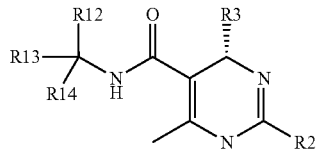
(V)

or in the presence or absence of a base or acid, at a temperature of 20-150° C., and in a suitable inert solvent, reacting a compound of formula (VI) or (VII)

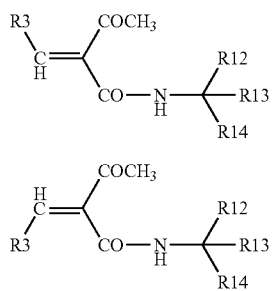
(VI)
(VII)

wherein $R^3$, $R^{12}$, $R^{13}$, $R^{14}$ are defined as above, with
the compound of formula (II), or
in the presence of an ammonium salt, reacting the aldehyde of formula (III) with the compound of formula (IV) and an iminoether of formula (VII)

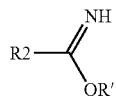
(VIII)

wherein $R^2$ is defined as above, and R' is $C_1$-$C_4$ alkyl.

2) acylating the compound of formula (V) in a suitable solvent, to obtain a compound of formula (IX)

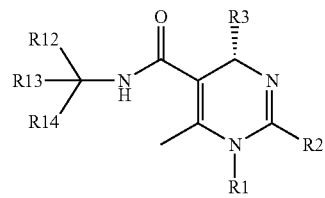
(IX)

wherein $R^1$ is ($C_1$-$C_6$)-acyl, arylacyl or arylsulfonyl, $R^2$, $R^3$, $R^{12}$, $R^{13}$, $R^{14}$ are defined as above, 3) the compound of formula (IX) is nitrosylated under an acidic or basic condition in a suitable solvent, and then reacted with sodium an alkoxide $R^{11}$ONa to obtain a compound of formula (I)

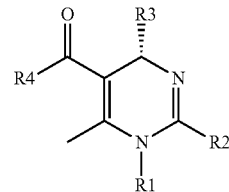
(X)

wherein $R^1$ is hydrogen, $R^2$, $R^3$, $R^4$, $R^{11}$ are defined as above.

The process of the present invention is exemplified by using the following reaction schemes:

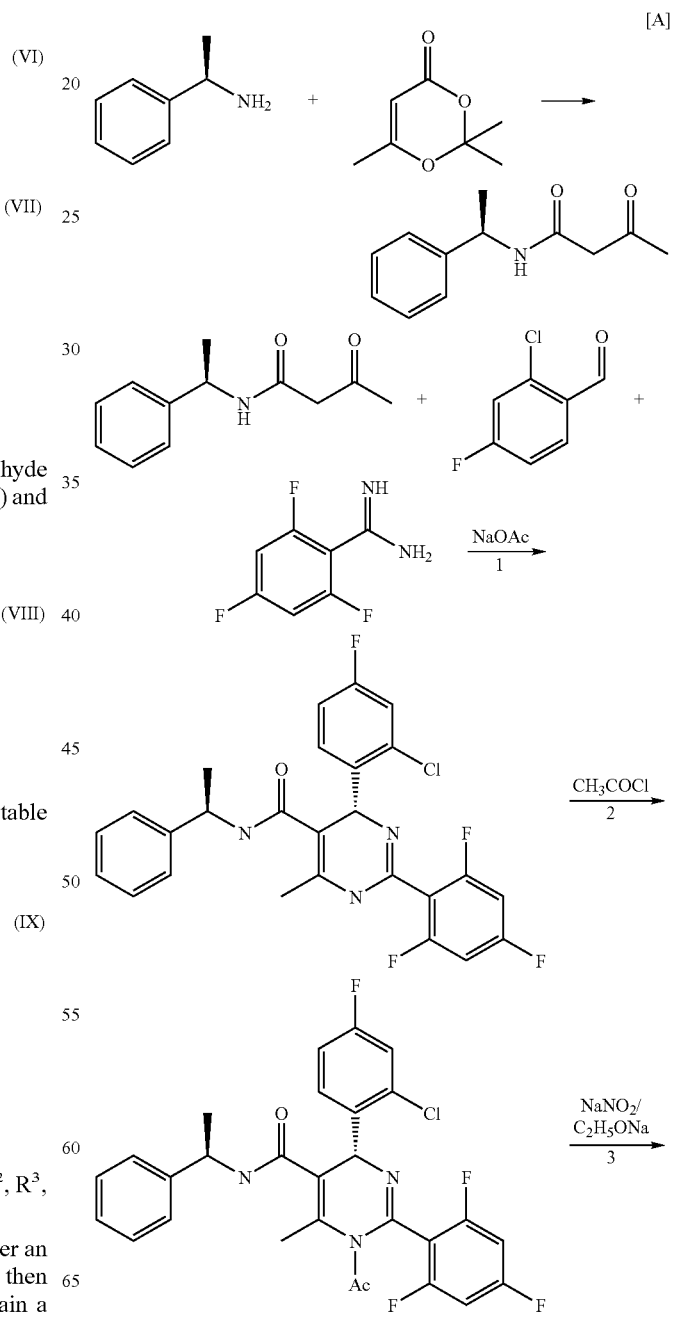
[A]

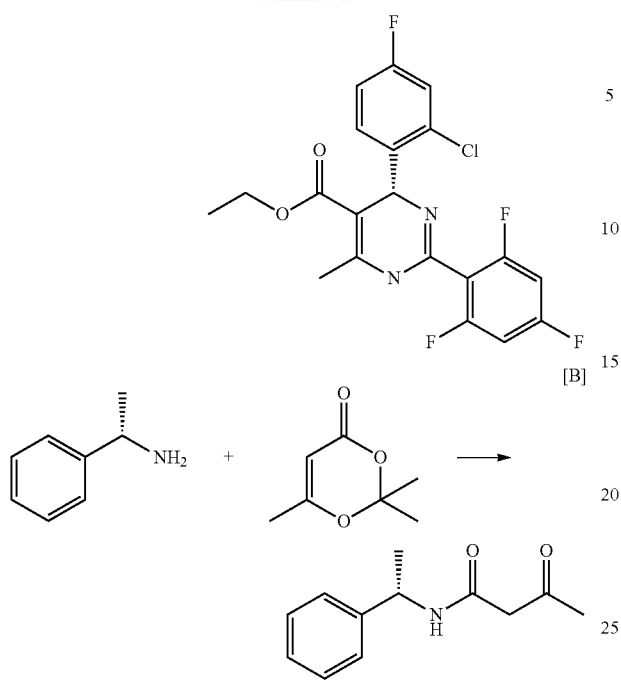
[B]
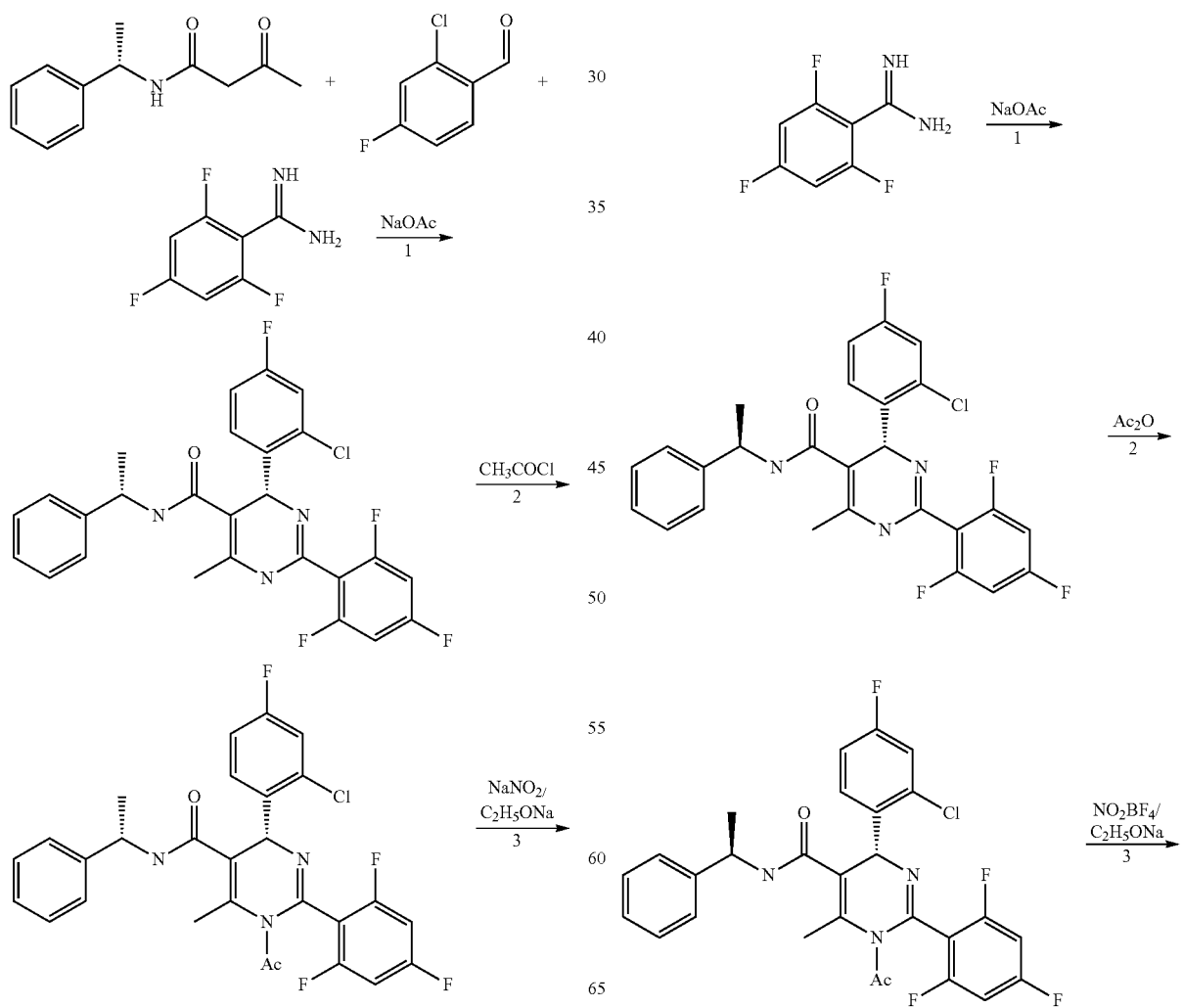
[C]

-continued

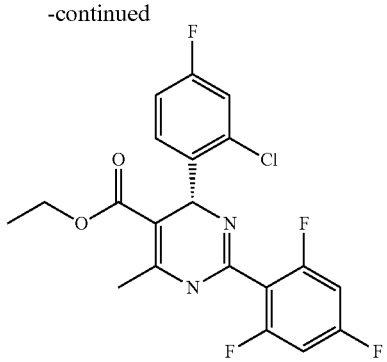

1. As to all of the reaction schemes A, B and C, suitable solvents in reaction step 1) are any inert organic solvents. These solvents preferably include alcohols such as ethanol, methanol, isopropanol, ethers such as dioxane, ethyl ether, TETRAHYDROFURAN, ethylene glycol monomethyl ether, ethylene glycol dimethyl ether or glacial acetic acid, dimethylformamide, dimethyl sulfoxide, acetonitrile, pyridine and hexamethylphosphamide.

The reaction temperature may vary within a relatively broad range. Usually, the reaction is carried out at a temperature of 20-150° C., but it is preferably carried out at the boiling point of the solvent.

The reaction may be carried out under normal pressure, or under an elevated pressure. Usually, the reaction is carried out under normal pressure.

The reaction may be carried out in the presence or absence of a base or acid, but it is preferably carried out in the presence of a relatively weak acid such as acetic acid or formic acid in the present invention.

The amidine of formula (II) as the starting substance is known in certain cases, or may be prepared from the corresponding cyano compound according to known methods described in literatures (cf. Diana, G. D., Yarinsky, A., Zalay, E. S., et al. J. Med. Chem. 1969, 12(9):791-793; Garigipati, R. S. Tetrahedron. Lett. 1990, 31(14):1969-1972; Boere, R. J., Oakley, R. T., Read, R. V. J Organometal. Chem. 1987, 331: 161-167; Judkins, B. D., Allen, D. G., Cook, T. A. Synth. Commun. 1996, 26(23):4351-4367; Tommasi, R. A., Macchia, W. M., Parker, D. T. Tetrahedron. Lett. 1998, 39:5947-5950).

The aldehyde of formula (III) as the starting substance is known, or may be prepared according to known methods described in literatures (cf. T. D. Harris and G. P. Roth, J. Org. Chem. 1979, 44, 146; DE 2165260, July 1972; DE 24016.65, July 1974; Mijano et. al. CA 1963, 59, 13929c; E. Adler, H. D. Becker, Chem. Scand. 1961, 15, 849; E. P. Papadopoulos, M. Mardin, Ch. Issidoridis, J. Org. Chem. Soc. 1956, 78, 2543).

The compound of formula (IV) $CH_3COCH_2CONHR^{12}$ as the starting substance is prepared by reacting a primary amine $R^{12}NH_2$ having a chiral center in its molecule with a diketene or diketene acetone adduct in the presence or absence of a base, and in an inert solvent. Usually, the reaction is carried out at 50-150° C., preferably 80-100° C.

The compound of formula (VI) or the compound of formula (VII) as the starting substance may be prepared by reacting the compound of formula (IV) $CH_3COCH_2CONHR^{12}$ with the aldehyde of formula (III) in an inert solvent under the condition of adding an acid or base or not, according to known methods described in literatures (cf. G. Jones, "Knoevenagel Condensation", Organic Reaction, Vol. XV, pages 204—(1967)).

The iminoether of formula (VIII) as the starting substance is known, or may be prepared according to known methods described in literatures (cf. S. A. Glckman, A. C. Cope, J. Am. Chem. Soc. 1945, 67, 1017).

2. The suitable solvent for the acylation in reaction step 2) is any inert aprotic organic solvent. These solvents preferably include ethers such as dioxane, ethyl ether, TETRAHYDROFURAN, ethylene glycol dimethyl ether or dimethylformamide, dimethyl sulfoxide, acetonitrile, pyridine and hexamethylphosphamide.

The reaction temperature may vary within a relatively broad range. Usually, the reaction is carried out at a temperature of −20-100° C., but it is preferably carried out at room temperature.

The reaction is usually carried out under basic condition. The suitable base is preferably, but not limited to, inorganic base such as potassium carbonate, sodium carbonate, sodium bicarbonate, sodium hydroxide, potassium hydroxide, sodium acetate or organic base such as triethylamine, pyridine, hexahydropyridine, N,N-dimethylaminopyridine, morpholine, and etc.

3. The nitrosylation product in step 3) is usually prepared by reacting with sodium nitrite under acidic condition, e.g., in the presence of acetic acid, hydrochloric acid or sulfuric acid, or reacting with $NO_2BF_4$ or $NOBF_4$ under basic condition, e.g., in the presence of sodium acetate, pyridine, hexahydropyridine or N,N-dimethylaminopyridine.

The suitable solvent for the nitrosylation reaction is any inert organic solvents. These solvents preferably include, but not limited to, dioxane, ethyl ether, acetonitrile, dichloromethane, nitromethane, TETRAHYDROFURAN, ethylene glycol monomethyl ether, ethylene glycol dimethyl ether, glacial acetic acid, dimethylformamide, dimethyl sulfoxide, pyridine and hexamethylphosphamide.

The reaction is usually carried out under the protection of an inert gas, at a temperature of −50-50° C., preferably 0° C.

The nitrosylation product is usually not purified, but is directly reacted with sodium alkoxide $R^{11}ONa$ to obtain the product. The sodium alkoxide may be prepared by reacting a corresponding alcohol with metal sodium.

As for more detailed information about the preparation of the compound of formula (I), please see the examples.

The antiviral effection of the compound of the present invention is determined according to the methods described by Sells, et al in (M. A. Sells M. L. Chen G. Proc. Natl. Acad. Sci. 1987, 84, 1005-1009) and Korba, et al (B. E. Korba, J. L. Gerin Antiviral Research 1992, 19, 55-70).

The antiviral test was carried out in a 96-cell microtiter plate. The first column of the plate only contained a culture medium for growth and HepG 2.2.15 cells, as a control. First, a stock solution (50 mmol) of a test compound was dissolved in DMSO, and further diluted with a culture medium for growth for HepG 2.2.15 cells. Usually, the compound of the present invention was transferred by suction at a test concentration of 100 μg/ml (the first test concentration) to each cell of the second column of the microtiter plate, and then diluted with the culture medium for growth plus 2% fetal bovine serum (25 μL), by 2 times once, up to 210 times at the maximum.

Then, 225 μL of a suspension of HepG 2.2.15 cells ($5\times10^4$ cells/ml) in the culture medium fro growth plus 2% fetal bovine serum was added to each pore of the 96-cell microtiter plate.

The test mixture was incubated under the conditions of 37° C., 5% $CO_2$ for 4 days. Then, the supernatant was removed by suction, and to each pore 225 μL of a new-prepared culture medium was added. Again, the compound of the present invention was added by a solution of 25 μL. The obtained mixture was further incubated for 4 days.

Prior to collection of the supernatant for determination of the antiviral effect, the cytotoxicity variation of HepG 2.2.15 cells was investigated by using optical microscopic technique or biochemical test method (e.g., Alamar Blue dyeing or Trypan Blue dyeing).

Thereafter, the supernatant was collected, and sucked in vacuum to a 96-cell dot blot chamber covered by nylon film (used in accordance with the directions for use given by the manufacturer).

Determination of Cytotoxicity

The substance-induced change in cytotoxicity in HepG 2.2.15 cells or change in inhibition of the cells could be determined by using, e.g., optical microscopic technique, and expressed by the change of cell morphology. Such substance-induced change, e.g., cell lysis, vacuolus formation or change in cell morphology, in HepG 2.2.15 cells was apparent as compared with the untreated cells. Taking the observed pathological change of cells as index, the pathological change of cells was observed under microscope after 8 days, a complete destroy being indicated as 4; 75% being indicated as 3; 50% being indicated as 2; 25% being indicated as 1; and no pathological change being indicated as 0. The average extents of pathological change of cells and the suppression percentages at various concentrations were calculated. According to Reed & Muench method, a half toxic concentration ($TC_{50}$) and a maximum non-toxic concentration ($TC_0$) were calculated.

$TC_{50}$ refers to the concentration of the compound of the present invention when 50% of cells have a similar morphology to the corresponding cells as a control.

Determination of Antiviral Activity

After the supernatant was transferred onto the nylon film of the dot blot device (as described above), the supernatant of HepG 2.2.15 cells was denaturated (1.5 M NaCl/0.5 M NaOH), neutralized (3 M NaCl/0.5 M Tris. HCl, pH 7.5) and washed (2×SSC). Then, the filter film was kept at 120° C. for 2-4 hours, whereby DNA was baked on the filter film.

DNA Hybridization

Usually, viral DNA of HepG 2.2.15 cells treated on the nylon filter film was detected by using a non-radioactive digoxigenin labelled type B hepatitis-specific DNA probe. Wherein, each time the probe was labelled with digoxigenin, purified and hybridized according to the directions for use given by the manufacturer.

Briefly, pre-hybridization and hybridization were conducted with 5×SSC, 1× blocking agent, 0.1% N-lauroyl sarcosine, 0.02% SDS and 100 μg sperm DNA of black carp. After pre-hybridization at 60° C. for 30 min, a specific hybridization (at 60° C. for 14 hr) was conducted with 20-40 ng/ml digoxigenin labelled denaturated I-BV specific DNA. Then, the filter film was washed, followed by digoxigenin antibody detection for HBV DNA.

The immunology detection of digoxigenin labelled DNA was conducted according to the directions for use given by the manufacturer.

Briefly speaking, the film was washed and pre-hybridized with a blocking agent (in accordance with the directions for use given by the manufacturer), and then hybridized with an anti-DIG antibody that had been previously coupled onto an alkaline phosphatase for 30 min. After washing, an alkaline phosphatase substrate CSPD was added, and cultured together with the filter for 5 min, and then wrapped in a plastic film, followed by further culturing at 37° C. for 15 min. The filter was exposed to X-ray, and the chemical luminous signal (culturing for 10 min to 2 hr according to the signal strength) of type B hepatitis-specific DNA on the film was detected, whereby a half inhibitory concentration ($IC_{50}$) was calculated.

The half inhibitory concentration ($IC_{50}$) refers to the concentration of the compound of the present invention which reduces the type B hepatitis-specific band by 50% as compared with the untreated sample.

The compound of the present invention exhibits a relatively strong antiviral effect. This kind of compound has unexpected antiviral activity to type B hepatitis virus (HBV), and thus is adapted to be used for treating various virus-caused diseases, in particular acute and chronic permanent diseases caused by HBV viral infection. Chronic viral diseases caused by HBV may lead to various syndromes having different extents of severity. As well known, chronic HBV infection may lead to hepatic cirrhosis and (or) liver cell carcinoma.

Examples of indications capable of being treated by the compound of the present invention include: acute and chronic viral infections capable of leading to infectious hepatitis, such as type B hepatitis viral infection, and particularly preferred chronic type. B hepatitis viral infection and acute type B hepatitis viral infection.

The pharmaceutical composition comprising the compound of the present invention may be administered by any of the following routes: orally, inhaled by spray, rectally, nasally, vaginally, topically, parenterally such as subcutaneous, intravenous, intramuscular, intraperitoneal, intrathecal, intraventricular, intrasternal or intracranial injection or infusion, or administered with the aid of an explanted reservoir, wherein the administration routes by orally, intramuscular, intraperitoneal or intravenous injection are preferred.

The compound of the present invention or the pharmaceutical composition comprising the compound of the present invention may be administered in a unit dosage form. The dosage form may be in a liquid form, or a solid form. The liquid form includes true solution, colloids, particulates, emulsions, suspensions. Other forms include, for example, tablets, capsules, dropping pills, aerosols, pills, powder, solutions, suspensions, emulsions, granules, suppository, lyophilized powder for injection, clathrates, implants, patches, liniment, and etc.

The pharmaceutical composition of the present invention may further comprise a commonly used carrier that includes, but not limited to, ion exchanger, alumina, aluminum stearate, lecithin, serum protein such as human serum protein, buffer such as phosphate, glycerin, sorbic acid, potassium sorbate, a mixture of partial glycerine esters of saturated vegetable fatty acids, water, salt or electrolyte, such as protamine sulfate, disodium hydrogen phosphate, potassium hydrogen phosphate, sodium chloride, zinc salt, colloidal silica, magnesium trisilicate, polyvinylpyrrolidone, cellulose, polyethylene glycol, sodium carboxymethylcellose, polyacrylate, beeswax, lanolin, and etc. The amount of the carrier in the pharmaceutical composition may be 1% to 98% by weight, usually about 80% by weight. For the convenience, topical anesthetic, antiseptic, buffer and etc. may be directly dissolved in the carrier.

Oral tablets and capsules may comprise excipients e.g., binders such as syrup, Arabic gum, sorbitol, tragacanth, or polyvinylpyrrolidone, fillers such as lactose, sucrose, corn starch, calcium phosphate, sorbitol, aminoacetic acid, lubricant such as magnesium stearate, saponite, polyethylene glycol, silica, disintegrating agent such as potato starch, or acceptable moisturizing agent such as sodium lauryl sulfate. Tablets may be coated by using known methods in pharmaceutics.

Oral solution may be made as a suspension of water and oil, a solution, an emulsion, a syrup or an elixir, or made as a dried product to which water or other suitable medium is added before use. This liquid preparation may comprise conventional additives, e.g., suspending agent such as sorbitol, cellulose methyl ether, glucose syrup, gelatin, hydroxyethyl cellulose, carboxymethyl cellulose, aluminum stearate gel, hydrogenated edible oils and fats; emulsifying agent such as lecithin, sorbitan monooleate, Arabic gum; or non-aqueous carrier (possibly including edible oil), such as almond oil, grease such as glycerin, ethylene glycol, or ethanol; antiseptic such as methyl or propyl p-hydroxybenzoate, sorbic acid. If desired, a flavoring agent or a colorant may be added.

Suppository may comprise a conventional suppository substrate, such as cocoa butter or other glyceride.

For parenteral administration, the liquid dosage form is usually made of the compound and a sterilized carrier. The preferred carrier is water. According to the carrier selected and the drug concentration, the compound can be dissolved in the carrier or made into a suspension. When making an injection solution, the compound is firstly dissolved in water, and then filtered and sterilized before being packaged into an sealed bottle or ampoule.

For topical application on skin, the compound of the present invention may be made into a suitable form of ointment, lotion or cream, wherein the active ingredient is suspended or dissolved in one or more carrier(s). The carrier used for an ointment includes, but not limited to, mineral oil, liquid vaseline, white vaseline, propylene glycol, polyoxyethylene, polyoxypropylene, emulsified wax and water; the carrier used for a lotion and a cream includes, but not limited to, mineral oil, sorbitan monostearate, Tween 60, cetyl esters wax, hexadecylene aromatic alcohol, 2-octyl dodecanol, benzanol and water.

In the above preparations, the active compound of formula (I) exists in a concentration of about 0.1 to 99.5% by weight, preferably about 0.5 to 95% by weight, based on the total weight of the mixture.

The above preparations may further comprise other pharmaceutically active compounds, in addition to the compound of formula (I).

In general, it has been proved that, advantageously, whether in human medicine or in veterinary medicine, the total dose of the active compound of the present invention is about 0.5 to 500 mg every 24 hr, preferably 1 to 100 mg per kg body weight. If appropriate, the drug is administrated by single dose for multiple times, to thereby achieve the desired effect. The amount of the active compound in a single dose is preferably about 1 to 80 mg, more preferably 1 to 50 mg per kg body weight. Nevertheless, the dose may also be varied according to the type and body weight of the object to be treated, the nature and extent of severity of diseases, the type of the preparation and the administration manner of the drug, and the administration period or the time interval.

Concrete Modes for Carrying Out the Invention

The following examples are preferred embodiments of the present invention, and shall not be understood to limit the present invention in any manner.

The melting point of the compound was determined by using RY-1 melting point apparatus, the thermometer being not calibrated. Mass spectrum was determined by using Micromass ZabSpec high resolution mass spectrograph (resolution 1000). $^1$H NMR was determined by using JNM-ECA-400 NMR spectrometer with superconducting magnet, and frequently used is $^1$H NMR 400 MHz, $^{13}$C NMR 100 MHz.

EXAMPLES

Example 1

Preparation of (R,R)—N-(1-phenylethyl)-4-(2-chloro-4-fluorophenyl)-6-methyl-2-(2-thiazolyl)-1,4-dihydropyrimidin-5-carboxamide

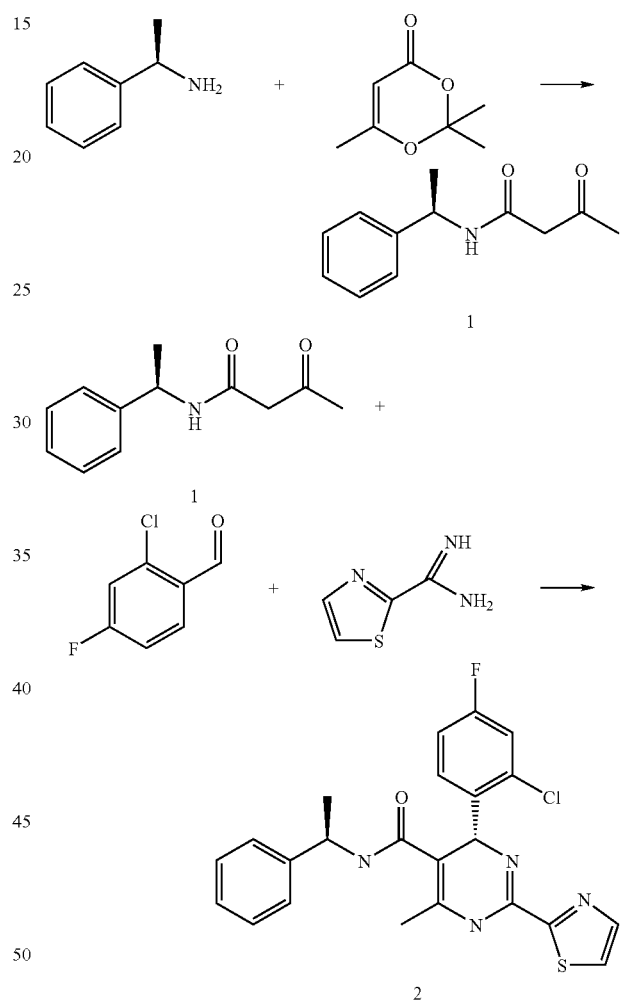

Step 1 6.06 g (50 mmol) (R)-α-methylbenzylamine and 7.11 g (50 mmol) diketene acetone adduct were placed in a 250 ml single-necked round flask, and then 100 ml N,N-dimethylformamide and 6.01 g (60 mmol) triethylamine were added, to carry out the reaction at 80-100° C. for 2 hr. After stopping the reaction, 200 ml water was added, and then the reaction mixture was neutralized with 4N hydrochloric acid to be neutral, and extracted with ethyl acetate. The obtained organic phase was washed with a saturated aqueous solution of sodium chloride, dried with anhydrous sodium sulfate, filtered, and concentrated to obtain 9.33 g compound 1 (yield 91%).

Step 2 4.5 g (22.05 mmol) compound 1, 3.5 g (22.05 mmol) 2-chloro-4-fluorobenzaldehyde, 4.5 g (22.05 mmol) 2-thiazol formamidine acetate and 1.0 g (22.05 mmol) anhydrous sodium acetate were added to 100 ml anhydrous ethanol, and reacted at reflux for 16 hr. The reaction mixture was concentrated to remove the solvent, and then the obtained solid was added to 40 ml ethyl acetate and 40 ml water and the layers were separated. The obtained water phase was extracted with 20 ml×2 ethyl acetate, and then the organic phases were combined, washed with a saturated aqueous solution of sodium chloride, dried with anhydrous sodium sulfate, filtered, concentrated, and separated by a flash column chromatography to obtain 2.93 g of a yellowish fine needle solid (compound 2) (yield 45%) with mp 224-226° C.; $^1$H-NMR (400 MHz, DMSO-d$_6$) δ 1.30-1.34 (3H, m); 2.01 (3H, s); 4.84-4.88 (1H, m); 5.97 (1H, s); 7.03-7.05 (2H, m); 7.12-7.24 (4H, m) 7.36-7.39 (1H, m); 7.49-7.53 (1H, m); 7.87-7.88 (1H, d); 7.93-7.96 (1H, m); 8.17-8.19 (1H, d) 9.35 (1H, s); MS (EI) 454.0 (M$^+$).

Example 2

Preparation of (R)-4-(2-chloro-4-fluorophenyl)-6-methyl-2-(2-thiazolyl)-1, 4-dihydropyrimidin-5-ethylcarboxylate

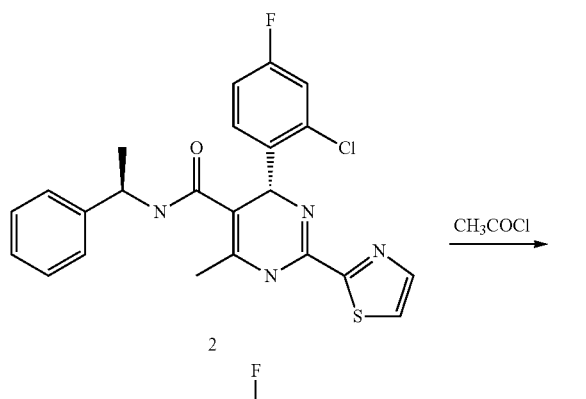

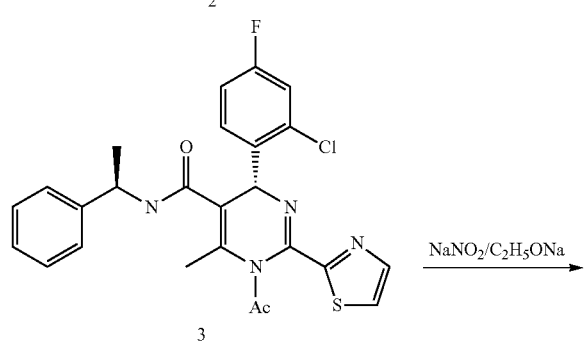

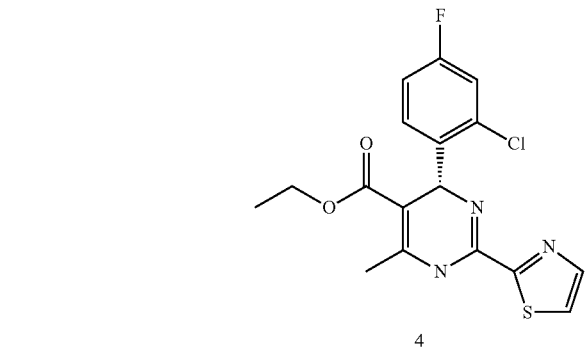

0.91 g (2 mmol) compound 2 was dissolved in 20 ml anhydrous N,N-dimethylformamide, 0.3 g (3 mmol) triethy-lamine was added, and 0.16 ml (2.4 mmol) acetyl chloride was added dropwise, to carry out the reaction at room temperature for 6 hr. 20 ml water was added to the reaction mixture, and then the reaction mixture was extracted with 15 ml×6 ethyl acetate. The obtained organic phase was washed with a saturated aqueous solution of sodium chloride, dried with anhydrous sodium sulfate, and separated by a flash column chromatography to obtain 0.746 g of compound 3 (yield 75%) with $^1$H-NMR (400 MHz, DMSO-d6) δ 1.23-1.41 (3H, m); 1.98 (3H, s); 2.17 (3H, s); 4.96-5.0 (1H, m); 6.59 (1H, s); 7.07-7.42 (8H, m); 7.98-7.99 (1H, d) 8.02-8.03 (1H, d) 8.63-8.64 (1H, d); MS (EI) 496.1 (M$^+$).

Under the protection of nitrogen, 0.5 g (1 mmol) compound 3 was placed in a 25 ml three-necked round flask, dissolved with 5 ml acetic acid, and cooled down in an ice bath, and then 0.14 g (2 mmol) sodium nitrite was added at 0° C., to carry out the reaction for 6 hr. 30 ml water was added to the reaction mixture, and then the reaction mixture was rapidly extracted with 15 ml×3 cold dichloromethane; the organic phase was washed with a saturated aqueous solution of sodium chloride, dried with anhydrous sodium sulfate, filtered, and concentrated to obtain 0.521 g of a product, which was not purified but was directly subjected to the subsequent reaction.

0.521 g of the above product was added to 15 ml anhydrous ethanol, and cooled in an ice bath, and then 0.135 g sodium ethoxide was added to carry out the reaction at 0° C. for 50 min. After stopping the reaction, 15 ml water was added, and then the reaction mixture was neutralized with 4N hydrochloric acid to be neutral, concentrated, and added ethyl acetate and water and the layers were separated. The obtained water phase was further extracted with 10 ml×3 ethyl acetate, and then the organic phases were combined, dried with anhydrous sodium sulfate, and separated by column chromatography to obtain 0.296 g of compound 4 (yield 78%), $^1$H-NMR (400 MHz, DMSO-d$_6$) δ 1.01-1.07 (3H, m); 2.46 (3H, s); 3.90-3.95 (2H, m); 5.99 (1H, s); 7.17-7.22 (1H, m); 7.90-7.91 (1H, d); 7.97-7.98 (1H, d); 9.96 (1H, s); MS (EI) 379.0 (M$^+$)

[α]$_D$=−54.6 (c=1%, CH$_3$OH).

Example 3

Preparation of (R)-4-(2-chloro-4-fluorophenyl)-6-methyl-2-(2-thiazolyl)-1, 4-dihydropyrimidin-5-trifluoroethylcarboxylate

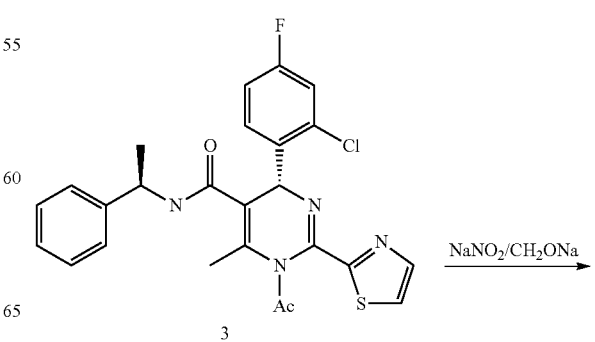

-continued

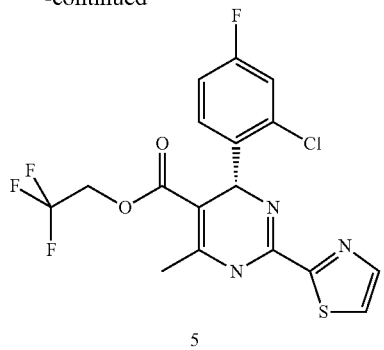

5

According to the method of Example 2, while using sodium trifluoroethoxide in place of sodium ethoxide, 0.296 g of a yellow amorphous solid compound 5 was obtained (yield 78%), $^1$H-NMR (400 MHz, DMSO-$d_6$) δ 4.60-4.64 (2H, m); 6.01 (1H, s); 7.16-7.21 (1H, m); 7.34-7.43 (2H, m); 7.92-7.93 (1H, d); 7.98-7.99 (1H, d); 10.23 (1H, s); MS (EI)-432.1 (M$^+$) [α]$_D$=−80.1 (c=1%, CH$_3$OH).

Example 4

Preparation of (R,R)—N-(1-phenylethyl)-4-(2-chloro-4-fluorophenyl)-6-methyl-2-(2,4,6-trifluorophenyl)-1,4-dihydropyrimidin-5-carboxamide

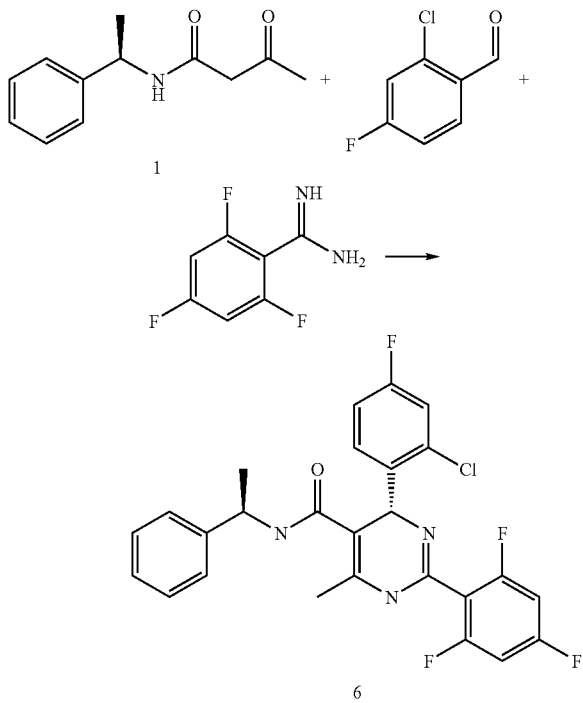

1.58 g (10 mmol) 2-Chloro-4-fluorobenzaldehyde and 2.04 g (10 mmol) compound 1 were dissolved in 40 ml ethanol, and stirred at room temperature for 2 d; then, 2.34 g (10 mmol) 2,4,6-trifluorobenzamidine acetate was added to react by reflux overnight; the reaction product was evaporated to remove the solvent, and then added ethyl acetate and water and the layers were separated. The obtained organic phase was dried with anhydrous sodium sulfate, filtered, concentrated, and separated by column chromatography to obtain 4.7 g of a mixture. The mixture was dissolved in ethyl acetate, to precipitate a solid compound 6, which was then recrystallized with 50% ethanol to obtain 2.2 g of a colorless fine needle solid. $^1$H-NMR (400 MHz, DMSO-$d_6$) δ 1.3-1.33 (3H, m); 1.97 (3H, s); 4.81-4.88 (1H, m); 5.96 (1H, s); 7.04-7.39 (9H, m); 7.57-7.61 (1H, m); 8.11-8.13 (1H, d); 9.25 (1H, s); MS (EI) 501 (M$^+$).

Example 5

Preparation of (R)-4-(2-chloro-4-fluorophenyl)-6-methyl-2-(2,4, 6-trifluorophenyl)-1,4-dihydropyrimidin-5-ethylcarboxylate

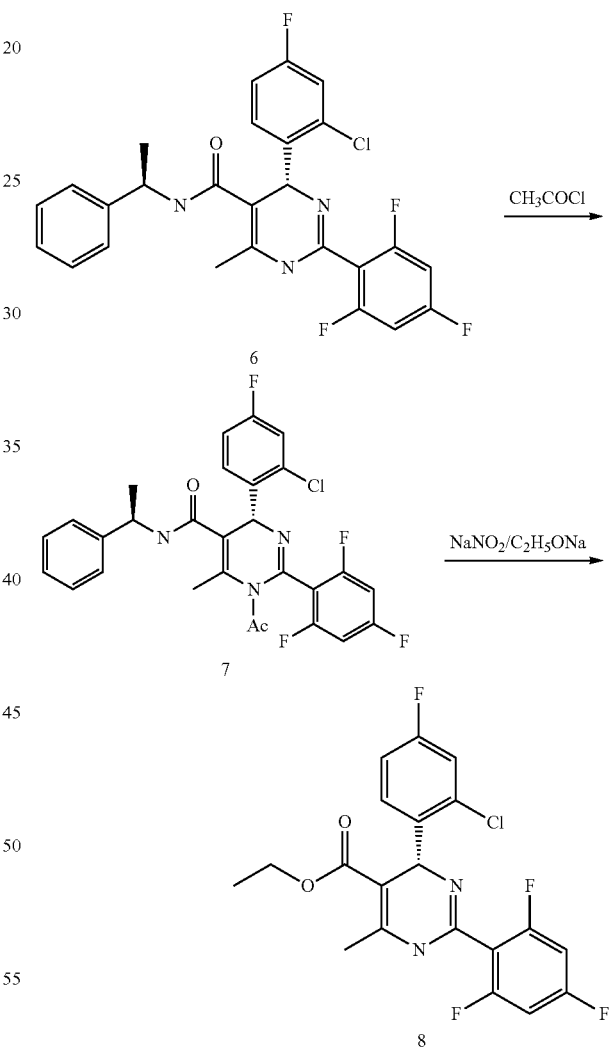

According to the method of Example 2, compound 6 was subjected to the reaction to prepare compound 7 as a colorless fine needle crystal. $^1$H-NMR (400 MHz, DMSO-$d_6$) δ 1.39-1.41 (3H, d, J=7.0); 2.07 (3H, s); 2.10 (3H, s); 4.95-4.99 (1H, m); 6.47 (1H, s); 7.08-7.30 (8H, m); 7.45-7.51 (2H, m); 8.70-8.72 (1H, d, J=8.12); MS (EI) 543 (M$^+$).

Compound 7 was subjected to the reaction to prepare compound 8 as a colorless fine needle crystal. mp 162-165° C.;

$^1$H-NMR (400 MHz, DMSO-d$_6$) δ 1.02-1.05 (3H, t, J=7.0 Hz); 2.32 (3H, s); 3.92-3.96 (2H, m, J=7.0 Hz); 5.97 (1H, s); 7.21-7.45 (5H, m); 9.86 (1H, s); MS (EI) 426 (M$^+$); [α]$_D$=−92.38 (c=1%, methanol).

Example 6

Preparation of (S,R)—N-(1-phenylethyl)-4-(2-chloro-4-fluorophenyl)-6-methyl-2-(5-thiazolyl)-1,4-dihydropyrimidin-5-carboxamide

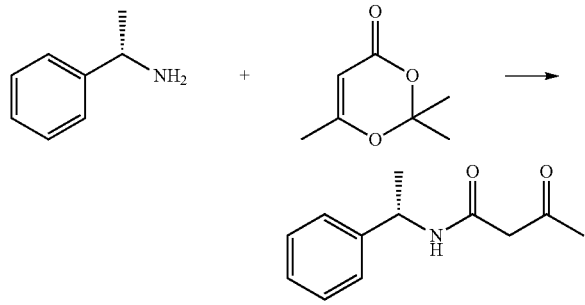

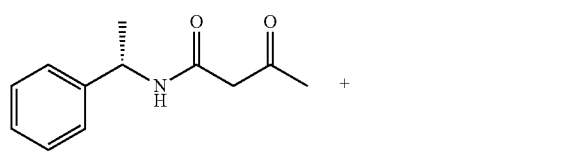

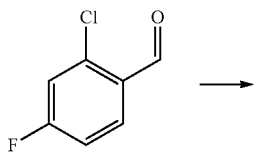

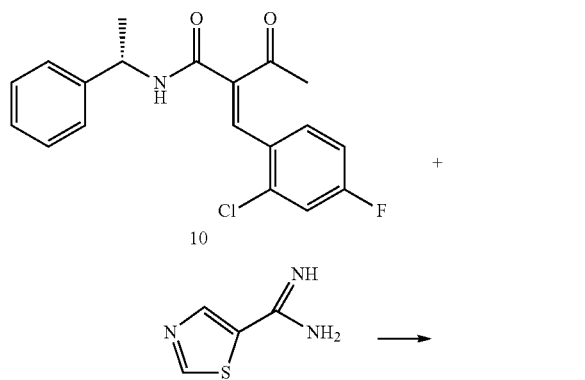

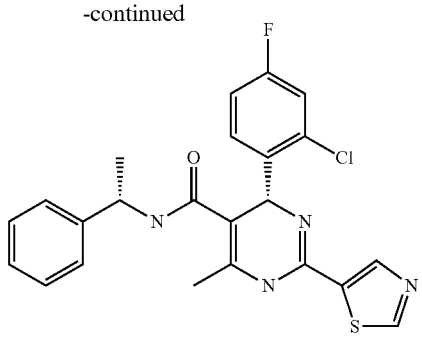

According to the method of Example 1, 6.1 g (50 mmol) (S)-α-methylbenzylamine was subjected to the reaction to obtain 9.6 g compound 9 (yield 95%).

2.9 g (14.2 mmol) compound 9 and 2.2 g (14.2 mmol) 2-chloro-4-fluorobenzaldehyde were dissolved in 50 ml anhydrous ethanol, and then acetic acid and hexahydropyridine were respectively added by 7 drops, to carry out the reaction at room temperature for 24 hr. The reaction mixture was concentrated, and separated by column chromatography to obtain 4.1 g of compound 10 as a white solid, which was recrystallized with ethyl acetate/petroleum ether.

$^1$H-NMR (400 MHz, CDCl$_3$) δ 1.42-1.44 (3H, d); 2.45 (3H, s); 5.18-5.21 (1H, m); 6.07-6.09 (1H, d); 6.72-6.76 (1H, m); 7.12-7.47 (9H, m); 7.75 (1H, s).

3.4 g (10 mmol) compound 10, 1.9 g (10 mmol) 5-thiazol formamidine acetate and 1.0 g (12 mmol) sodium acetate were dissolved in 50 ml anhydrous ethanol, and reacted at reflux for 20 hr. The reaction mixture was concentrated to remove the solvent, and then the obtained solid was added to ethyl acetate and water and the layers were separated. The obtained water phase was further extracted with ethyl acetate, and the obtained organic phases were combined, washed with a saturated aqueous solution of sodium chloride, dried with anhydrous sodium sulfate, filtered, concentrated, and separated by column chromatography to obtain 1.9 g of a yellowish solid (compound 11) with the yield of 41%.

$^1$H-NMR (400 MHz, DMSO-d$_6$) δ 1.22-1.25 (3H, m); 2.11 (3H, s); 4.85-4.88 (1H, m); 5.96 (1H, s); 7.14-7.43 (8H, m); 8.10-8.12 (1H, d); 8.49 (1H, s); 9.09 (1H, s); 9.17 (1H, s) MS(EI) 454.0 (M$^+$).

Example 7

Preparation of (R)-4-(2-chloro-4-fluorophenyl)-6-methyl-2-(5-thiazolyl)-1,4-dihydropyrimidin-5-ethylcarboxylate

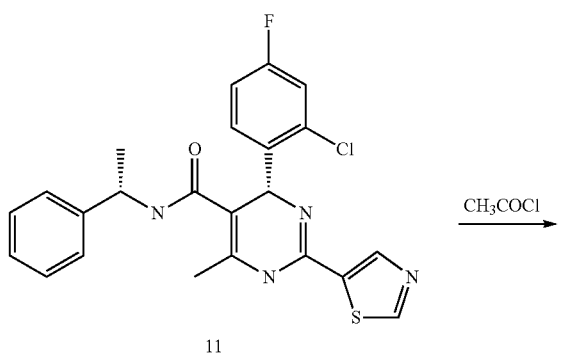

23

-continued

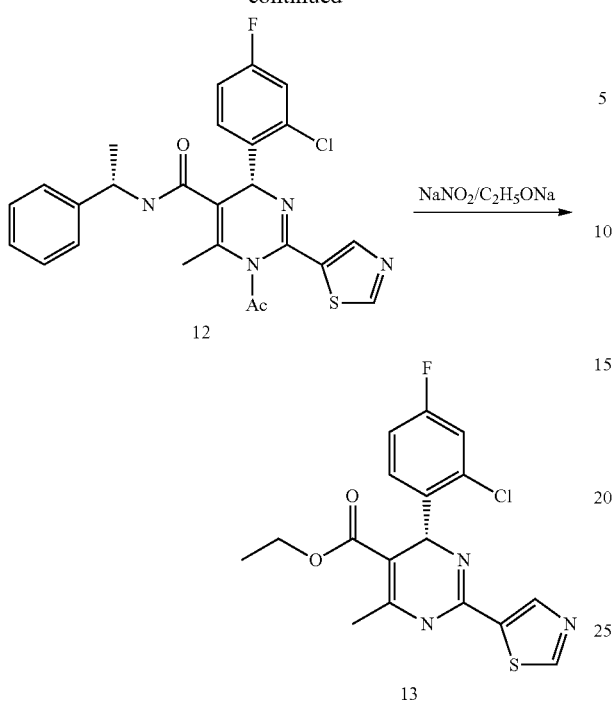

According to the method of Example 2, compound 11 was subjected to the reaction to prepare compound 12 as a yellow foam solid. $^1$H-NMR (400 MHz, DMSO-d$_6$) δ 1.34-1.36 (3H, d); 2.08 (3H, s); 2.18 (3H, s); 4.97-5.01 (1H, m); 6.56 (1H, s); 7.11-7.37 (7H, m); 7.50-7.53 (1H, dd); 7.93 (1H, s); 8.72-8.74 (1H, d); 9.23 (1H, s); MS (EI) 496.1 (M$^+$).

Compound 12 was subjected to the reaction to prepare compound 13. $^1$H-NMR (400 MHz, DMSO-d$_6$) δ 1.0-1.06 (3H, t, J=7.0 Hz); 2.44 (3H, s); 3.92-3.94 (2H, m, J=7.0 Hz); 5.93 (1H, s); 7.36-7.39 (3H, m); 8.54 (1H, s); 9.11 (1H, s); 9.60 (1H, s); MS (EI) 379.0 (M$^+$);

$[\alpha]_D$=−65.0 (c=1%, methanol).

Example 8

Determination of Cytotoxicity and Antiviral Activity of the Compounds

The cytotoxicity and antiviral activity of the compounds according to this invention were determined in accordance with the methods described above, and the results were showed in Table 1.

TABLE 1

| Inhibitory actions of the compounds on HBV DNA | | |
|---|---|---|
| Example No. | IC$_{50}$ μM | TD$_{50}$ μM |
| 2 | <0.8 | >62.9 |
| 3 | 5.1 | 37.4 |
| 5 | 1.3 | 13.8 |
| 7 | 1.8 | >12.5 |

24

What is claimed is:

1. A process for preparing an optically pure compound of formula (I),

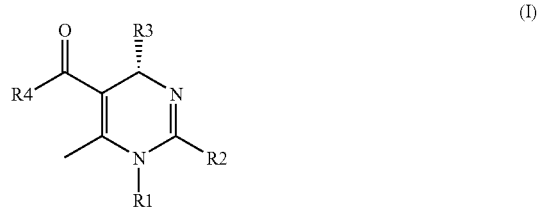

wherein

R$^1$ represents hydrogen,

R$^2$ represents phenyl optionally substituted up to 5 times by fluoro, or thiazolyl optionally substituted by one or more substituents which are the same or different, and selected from: fluoro, chloro, bromo, (C$_1$-C$_3$)-alkyl, (C$_1$-C$_3$)-alkoxy, amino, and (C$_1$-C$_3$)-acylamino, R$^3$ represents phenyl, optionally substituted by one or more substituents which are the same or different, and selected from: fluoro, chloro, bromo, iodo, hydroxyl, trifluoromethyl, trifluoromethoxy, trifluoromethylsulfonyl, nitro, cyano, carboxy, and methoxycarbonyl, and R$^4$ represents a group represented by formula —OR$^{11}$, wherein R$^{11}$ represents hydrogen, (C$_1$-C$_3$)-alkenyl or (C$_1$-C$_4$)-alkyl, wherein the (C$_1$-C$_3$)-alkenyl and (C$_1$-C$_4$)-alkyl independently are optionally substituted by halogen, pyridyl, cyano, phenoxy, alkoxy, trifluoroethyl, benzyl or a group represented by formula —NR$^{15}$R$^{16}$, wherein R$^{15}$ and R$^{16}$, the same or different, respectively represent hydrogen, benzyl or methyl, or a pharmaceutically acceptable salt thereof, comprising the steps of:

1) reacting an amidine of formula (II) or a salt thereof

wherein R$^2$ is defined as above, with an aldehyde of formula (III)

wherein R$^3$ is defined as above, and a compound of formula (IV)

CH$_3$COCH$_2$CONHCR$^{12}$R$^{13}$R$^{14}$ (IV)

wherein R$^{12}$, R$^{13}$, R$^{14}$ are different and respectively represent a substituent selected from hydrogen, substituted or unsubstituted phenyl, benzyl, or a straight or branched (C$_1$-C$_3$)-hydrocarbyl, in the presence or absence of a base or acid, and in a suitable inert solvent, to obtain a compound of formula (V)

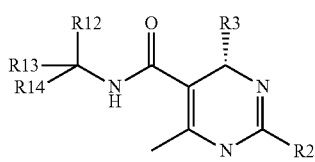

(V)

or
reacting a compound of formula (VI) or (VII)

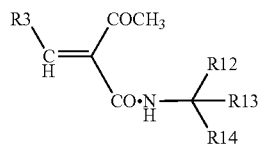

(VI)

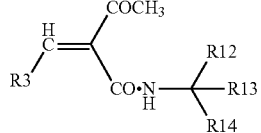

(VII)

wherein $R^3$, $R^{12}$, $R^{13}$, and $R^{14}$ are defined as above, with a compound of formula (II), in the presence or absence of a base or acid, at a temperature of 20-150° C., and in a suitable inert solvent, to obtain a compound of formula (V), or
reacting a aldehyde of formula (III) with a compound of formula (IV) and an iminoether of formula (VIII)

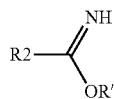

(VIII)

wherein $R^2$ is defined as above, and R' is $C_1$-$C_4$ alkyl, in the presence of an ammonium salt, to obtain a compound of formula (V), 2) acylating the compound of formula (V) in a suitable solvent, to obtain a compound of formula (IX)

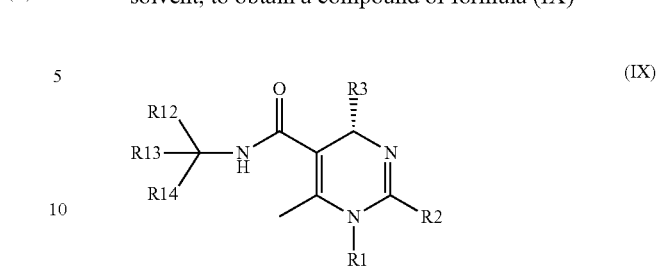

(IX)

wherein $R^1$ is $(C_1$-$C_6)$-acyl, arylacyl or arylsulfonyl, and $R^2$, $R^3$, $R^{12}$, $R^{13}$ and $R^{14}$ are defined as above, and 3) the compound of formula (IX) is nitrosylated under an acidic or basic condition in a suitable solvent, and then reacted with sodium alkoxide $R^{11}$ONa to obtain a optically pure compound of formula (I)

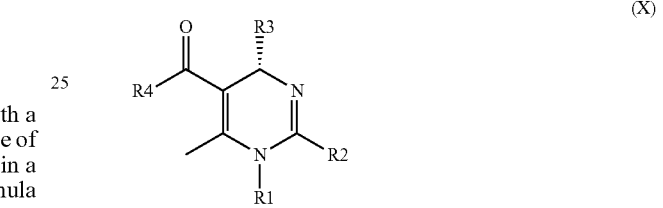

(X)

wherein $R^1$, $R^2$, $R^3$, and $R^4$ are defined as above.

2. The process of claim 1 wherein the compound of formula (IV) $CH_3COCH_2CONHCR^{12}R^{13}R^{14}$ is prepared by a process comprising reacting a chiral primary amine $R^{12}R^{13}R^{14}CNH_2$ with a diketene or diketene acetone adduct in the presence or absence of a base, and in an inert solvent, wherein $R^{12}$, $R^{13}$, and $R^{14}$ are as defined in claim 1.

3. The process of claim 1 further comprising transferring the compound of formula (I) into a pharmaceutically acceptable salt thereof.

\* \* \* \* \*